United States Patent [19]

Volkamer et al.

[11] 4,277,315

[45] Jul. 7, 1981

[54] ISOLATION OF A CONJUGATED DIOLEFIN FROM A $C_4$- OR $C_5$-HYDROCARBON MIXTURE

[75] Inventors: Klaus Volkamer, Frankenthal; Klaus Broellos, Seeheim; Alfred Lindner, Bobenheim-Roxheim; Ulrich Wagner, Limburgerhof; Hans-Martin Weitz, Bad Duerkheim; Klaus-Juergen Schneider, Neustadt, all of Fed. Rep. of Germany

[73] Assignee: BASF Aktiengesellschaft, Fed. Rep. of Germany

[21] Appl. No.: 126,897

[22] Filed: Mar. 3, 1980

[30] Foreign Application Priority Data

Mar. 23, 1979 [DE] Fed. Rep. of Germany ....... 2911394

[51] Int. Cl.$^3$ ............................ B01D 3/40; C07C 7/08
[52] U.S. Cl. .......................................... 203/51; 203/53; 203/58; 203/60; 585/810; 585/862; 585/865; 585/866
[58] Field of Search ...................... 203/60, 51, 54, 55, 203/56, 58, 53; 585/864–866, 862, 810

[56] References Cited

U.S. PATENT DOCUMENTS

| | | | |
|---|---|---|---|
| 2,366,360 | 1/1945 | Semon | 203/56 |
| 2,426,821 | 9/1947 | Evans et al. | 203/60 |
| 3,031,515 | 4/1962 | Deprez et al. | 203/60 |
| 3,206,377 | 9/1965 | Cornell et al. | 203/60 |
| 3,242,227 | 8/1972 | Kroeper et al. | |
| 3,436,438 | 4/1969 | Takao et al. | |
| 3,681,202 | 8/1972 | Funkhouser | 203/60 |
| 4,081,332 | 3/1978 | Hein | 203/56 |

OTHER PUBLICATIONS

The Soviet Chemical Industry, No. 11, Nov. 1971, pp. 719–723.

Primary Examiner—Wilbur L. Bascomb, Jr.
Attorney, Agent, or Firm—Keil & Witherspoon

[57] ABSTRACT

A process for isolating a conjugated diolefin from a $C_4$- or $C_5$-hydrocarbon mixture containing the diolefin, by single-stage or multi-stage extractive distillation using a selective solvent, wherein the selective solvent is a solvent mixture which comprises (a) from 1 to 99 percent by weight of an N-alkyl-substituted lower aliphatic acid amide or of an N-alkyl-substituted alicyclic acid amide having 5 ring members and (b) from 1 to 99 percent by weight of an lower aliphatic carboxylic acid ester or carbonic acid ester boiling at from 30° C. to 200° C.

3 Claims, No Drawings

ISOLATION OF A CONJUGATED DIOLEFIN FROM A C$_4$- OR C$_5$-HYDROCARBON MIXTURE

The present invention relates to a process for isolating a conjugated diolefin from a C$_4$- or C$_5$-hydrocarbon mixture by extractive distillation with the aid of a selective solvent.

Extractive distillation is a known process for separating mixtures which are not easily separable by conventional fractional distillation, for example if the components to be separated form an azeotrope or if the differences in the relative volatilities are slight. In extractive distillation, a solvent of relatively low volatility is introduced into the distillation column in such amounts that the differences in the relative volatilities of the components to be separated are increased and hence distillative separation becomes possible. Typical examples of the application of extractive distillation are to be found, for instance, in C. S. Robinson et al. "Elements of Fractional Distillation", 4th edition, McGraw-Hill Book Company, Inc., New York, (1959), page 291.

It is known, for example from German Published Application DAS No. 1,568,902, German Patent No. 1,163,795 or The Soviet Chemical Industry, No. 11, November 1971, pages 719–723, that conjugated diolefins can be isolated from a C$_4$- or C$_5$-hydrocarbon mixture by extractive distillation using a selective solvent. The selective solvents can be used substantially anhydrous. However, in this method, which is used especially in the case of solvents sensitive to hydrolysis, the C$_4$- or C$_5$-hydrocarbon selectivity is in general insufficient. Hence, water has been added to the selective solvents to increase the selectivity and to lower the boiling point. However, such addition of water to the selective solvent has the disadvantage that it reduces the solubility of the C$_4$- or C$_5$-hydrocarbons in the selective solvent, so that the amount of selective solvent circulating in the extraction unit is correspondingly increased.

It is an object of the present invention to provide a process for isolating a conjugated diolefin from a C$_4$- or C$_5$-hydrocarbon mixture containing the diolefin, by single-stage or multi-stage extractive distillation using a selective solvent, wherein the amount of selective solvent circulating in the extraction unit can be kept low.

According to the invention, this object and other objects and advantages are achieved by a process for isolating a conjugated diolefin from a C$_4$- or C$_5$-hydrocarbon mixture containing the diolefin, by single-stage or multi-stage extractive distillation using a selective solvent, wherein the selective solvent used is a solvent mixture which comprises (a) from 1 to 99 percent by weight of an N-alkyl-substituted lower aliphatic acid amide or of an N-alkyl-substituted alicyclic acid amide having 5 ring members and (b) from 1 to 99 percent by weight of a lower aliphatic carboxylic acid ester or carbonic acid ester boiling at from 30° C. to 200° C.

The solubility of the C$_4$- or C$_5$-hydrocarbons in the solvent mixture which according to the invention is to be used as the selective solvent is substantially increased compared to the conventional processes, whilst the C$_4$- or C$_5$-hydrocarbon selectivity is similar, so that the amount of selective solvent circulating in the extraction unit for isolating the conjugated diolefin can be greatly reduced. This in particular results in a great reduction in the investment required for the extraction unit, and in the consumption of steam and electrical energy. Furthermore, the solvent mixture to be used according to the invention has a lower viscosity, a lower heat of vaporization and a lower specific heat than the conventional selective solvents of comparable C$_4$- or C$_5$-hydrocarbon selectivity. The lower viscosity of the solvent mixture to be used according to the invention results in a higher tray efficiency in the extractive distillation column, whilst as a result of the lower heat of vaporization and lower specific heat, energy can additionally be saved.

If a mixture of one of the relatively high-boiling solvents according to section (a) above with a solvent according to section (b) which is lower-boiling than the first-mentioned solvent is used, for example if the solvent according to section (b) boils below 150° C., preferably below 120° C., an additional advantage achieved is that the solvent recovery zone of the extraction unit for isolating the conjugated diolefin, which recovery zone is, for example, operated as a degassing zone or solvent stripper zone, can, for a given bottom temperature, be operated under higher pressure than is the case when using only the solvents according to (a) in accordance with conventional processes. This has the advantage, for example, that because of the higher pressure the degassed hydrocarbons obtained in the solvent recovery zone can in a simple manner, and without interpolation of a compressor or blower, be fed into downstream zones operated under higher pressure. Another advantage of using a mixture of one of the relatively high-boiling solvents according to (a) above with a lower-boiling solvent according to (b) above is that the solvent recovery zone of the extraction unit, which zone is, for example, operated as a degassing zone or solvent stripping zone, can, when using the same pressure as in conventional processes, be operated at a lower bottom temperature, so that contamination of the extraction unit by polymer formation can more easily be avoided.

The process according to the invention employs a solvent mixture which comprises (a) from 1 to 99 percent by weight of an N-alkyl-substituted lower aliphatic acid amide or of an N-alkyl-substituted alicyclic acid amide having 5 ring members and (b) from 1 to 99 percent by weight of a lower aliphatic carboxylic acid ester or carbonic acid ester boiling at from 30° C. to 200° C., preferably from 40° C. to 150° C., especially from 50° C. to 120° C.

Examples of suitable N-alkyl-substituted lower aliphatic acid amides are dimethylformamide, diethylformamide, dimethylacetamide, diethylacetamide and formylmorpholine. Examples of suitable N-alkyl-substituted alicyclic acid amides (lactams) are N-alkylpyrrolidones, especially N-methylpyrrolidone. In general, N-alkyl-substituted lower aliphatic acid amides or N-alkyl-substituted alicyclic acid amides boiling at from 150° C. to 260° C., preferably from 150° C. to 210° C., are used. It is particularly advantageous to use dimethylformamide and more especially still N-methylpyrrolidone as the solvent (a).

The solvent mixture to be used according to the invention contains from 1 to 99 percent by weight, preferably from 2 to 50 percent by weight, especially from 3 to 20 percent by weight, of one of the solvents according to (b) above. Correspondingly, the solvent mixture contains from 1 to 99 percent by weight, preferably from 50 to 98 percent by weight, especially from 80 to 97 percent by weight, of one of the solvents according to (a) above. If a solvent mixture containing N-methylpyrrolidone is used, it particularly advantageously contains from 7 to 17 percent by weight of one of the solvents according to (b) above.

Examples of suitable lower aliphatic carboxylic acid esters are those derived from monocarboxylic acids of, in general, 1 to 4, preferably 1 to 3, carbon atoms, eg. formic acid, acetic acid and propionic acid, or from dicarboxylic acids of 2 or 3 carbon atoms, eg. oxalic acid or malonic acid. The alcohol component of the carboxylic acid esters is in general a monohydric alcohol of advantageously 1 to 6, preferably 1 to 4, carbon atoms, eg. methanol, ethanol, propanol, isopropanol, n-butanol or isobutanol, or from dihydric alcohols of, in general, 2 or 3 carbon atoms, eg. ethylene glycol and 1,2-propylene glycol. In the case of the carboxylic acid esters derived from dihydric alcohols, the monoester or, preferably, the diester may be used. Specific examples of suitable lower aliphatic carboxylic acid esters are formic acid esters, eg. methyl, ethyl, n-propyl, isopropyl, n-butyl, isobutyl, amyl and hexyl formate, ethylene glycol diformate and ethylene glycol monoformate, acetic acid esters, eg. methyl, ethyl, n-propyl, isopropyl, n-butyl, isobutyl, amyl and hexyl acetate and ethylene glycol diacetate, propionic acid esters, eg. methyl, ethyl, n-propyl, isopropyl, n-butyl, isobutyl, amyl and hexyl propionate, oxalic acid esters, eg. dimethyl oxalate and diethyl oxalate, and malonic acid esters, eg. dimethyl malonate and diethyl malonate. Suitable carbonic acid esters are the unsymmetrical and, preferably, the symmetrical esters, in general derived from monohydric alcohols of 1 to 4 carbon atoms, eg. from methanol, ethanol, propanol, isopropanol, n-butanol and isobutanol. Specific examples of suitable carbonic acid esters are dimethyl, diethyl, diisopropyl, di-n-propyl, diisobutyl and di-n-butyl carbonate. In addition to the pure esters, their mixtures (including, in the case of diesters of dihydric alcohols, mixtures containing the monoester) may be used.

The solvent mixture to be used according to the invention can contain a small amount of water, for example up to 10 percent by weight. Advantageously, however, the water content is restricted to at most 5 percent by weight, preferably at most 3 percent by weight, based on the solvent mixture. However, it can be advantageous to employ a substantially anhydrous solvent mixture, ie. a mixture containing at most 1 percent by weight, preferably at most 0.5 percent by weight, in particular at most 0.1 percent by weight, of water, based on the solvent mixture.

The isolation of a conjugated diolefin from a $C_4$- or $C_5$-hydrocarbon mixture containing the latter, using the solvent mixture which according to the invention is employed as the selective solvent, is carried out in a conventional manner (cf., for example, German Patent No. 1,184,334 and German Published Applications DAS Nos. 1,568,876 and 1,568,902) by single-stage or multi-stage, advantageously single-stage or two-stage, extractive distillation. For example, the conjugated diolefins, eg. 1,3-butadiene, isoprene and 1,3-pentadiene, are isolated from the $C_4$- or $C_5$-hydrocarbon mixture by subjecting the latter, which contains both hydrocarbons which are more soluble and hydrocarbons which are less soluble than the conjugated diolefin, to an extractive distillation with the solvent mixture to be used according to the invention, from which distillation a distillate containing the less soluble hydrocarbons and an extract containing the conjugated diolefin, the more soluble hydrocarbons and the selective solvent are obtained. The conjugated diolefin can be isolated, from the extract, in the form of a crude product which is of adequate purity for certain applications, but which can also be subjected to additional purification operations, for example fractional distillation. Advantageously, however, the conjugated diolefin is isolated by using two successive extractive distillation stages using the solvent mixture to be employed according to the invention.

Using the latter method, the first stage of the extractive distillation results, for example, as already described above, in a distillate containing the less soluble hydrocarbons and an extract containing the conjugated diolefin, the more soluble hydrocarbons and the selective solvent. This extract is freed from the selective solvent, giving a mixture of the conjugated diolefin and the more soluble hydrocarbons. This mixture is subjected to a second extractive distillation using the selective solvent, giving the conjugated diolefin as the distillate, and an extract which contains the more soluble hydrocarbons and the selective solvent. The extract obtained is subsequently freed from the selective solvent, giving a hydrocarbon stream containing the more soluble hydrocarbons.

The hydrocarbon mixture, containing conjugated diolefins, used as the starting mixture for the process of the present invention may be a $C_4$- or $C_5$-fraction which was obtained by thermal cracking of a petroleum fraction (for example LPG, naphtha and the like), a butadiene-containing fraction obtained by dehydrogenation of n-butane and/or n-butene, or an isoprene-containing fraction obtained by dehydrogenation of isopentane and/or isoamylene. In general, the $C_4$-hydrocarbon mixture contains 1,3-butadiene as the conjugated diolefin, together with butanes, but-1-ene, trans-but-2-ene, cis-but-2-ene, isobutene, vinylacetylene, ethylacetylene and 1,2-butadiene, with or without small amounts of $C_3$- and/or $C_5$-hydrocarbons. The $C_5$-hydrocarbon mixture as a rule contains isoprene, trans- and cis-1,3-pentadiene and cyclopentadiene as conjugated diolefins, together with pentanes, n-pentenes, isoamylene, cyclopentene and higher acetylenes.

By way of example, extractive distillation of a $C_4$-fraction first gives a distillate containing the butanes and butenes, and an extract containing 1,3-butadiene, ethylacetylene, vinylacetylene and 1,2-butadiene, which extract, when subjected to a further extractive distillation, gives 1,3-butadiene as the distillate, whilst the extract contains ethylacetylene, vinylacetylene and 1,2-butadiene. The ethylacetylene, vinylacetylene and 1,2-butadiene are separated from the extract, containing these hydrocarbons, in a degassing unit, and the degassed solvent is recycled to the extractive distillation. The 1,3-butadiene obtained as the distillate can subsequently be subjected to a fractional distillation to remove the very small amounts of $C_3$- and/or $C_5$-hydrocarbons which may still be present.

The Examples which follow illustrate the invention.

EXAMPLE 1

Example 1 illustrates the single-stage extractive distillation of a $C_4$-hydrocarbon mixture.

A packed column of 25 mm internal diameter and 2.50 m height, operated under 1 bar at 15° C., is fed, at the bottom, with 0.768 kg/h of a C4-hydrocarbon mixture of the following composition:

| Composition | % by weight |
|---|---|
| i-Butane | 1.33 |
| n-Butane | 4.44 |
| But-1-ene | 11.65 |
| i-Butene | 28.21 |
| Trans-but-2-ene | 7.28 |
| Cis-but-2-ene | 4.45 |
| 1,3-Butadiene | 41.98 |
| 1,2-Butadiene | 0.31 |
| Ethylacetylene | 0.24 |
| Vinylacetylene | 0.11 |

At the top of the column, 4.60 kg/h of recycled selective solvent, containing 90% by weight of dimethylformamide and 10% by weight of ethyl acetate, are introduced at 15° C. 0.379 kg/h of a raffinate containing 2% by weight of 1,3-butadiene and 5.6% by weight of cis-but-2-ene are taken off as gas at the top of the column. At the bottom of the column, an extract containing the more readily soluble hydrocarbons is obtained, and this is degassed by feeding it to the top of a downstream column which has 10 bubble-cap trays and is operated at a bottom temperature of 130°–140° C. From the bottom of this column, the selective solvent, which has been substantially freed from the hydrocarbons, is recycled, after cooling, to the top of the packed column. At the center of the bubble-cap tray column, 0.389 kg/h of crude butadine containing 80.61% by weight of 1,3-butadiene and 3.3% by weight of cis-but-2-ene are taken off. The hydrocarbons issuing at the top of the bubble-cap tray column are recycled, as gas, to the bottom of the packed column. The ratio S/M of the circulating solvent S (4.60 kg/h) to the C4-hydrocarbon mixture feed M (0.768 kg/h) is 5.99.

COMPARATIVE EXPERIMENT

In a Comparative Experiment, the procedure described in Example 1 above is followed except that pure dimethylformamide is used as the selective solvent and the C4-hydrocarbon mixture is introduced into the bottom of the packed column in a lower amount than in Example 1, namely at the rate of 0.621 kg/h; 0.306 kg/h of raffinate and 0.315 kg/h of crude butadiene are obtained, ie. the C4-hydrocarbon mixture is divided into raffinate and crude butadiene in virtually the same ratio as in Example 1. The key components cis-but-2-ene and 1,3-butadiene have the same contents in the raffinate and crude butadiene in the Comparative Experiment as in Example 1. The S/M ratio of circulating solvent S (4.60 kg/h) to feed M of C4-hydrocarbon mixture (0.621 kg/h) is 7.41, i.e. in the Comparative Experiment the S/M ratio had to be about 23% higher than in Example 1 (S/M ratio 5.99) in order to achieve the same degree of success of the separation.

EXAMPLE 2

The procedure described in Example 1 and the corresponding Comparative Experiment is followed, except that in Example 2 the temperature is 5° C. higher, the selective solvent is a mixture of 90% by weight of N-methylpyrrolidone and 10% by weight of diethyl carbonate and the S/M ratio of circulating solvent S to feed M of C4-hydrocarbon mixture is maintained at 6.60, whilst in the Comparative Example accompanying Example 2, the selective solvent is a mixture of 91.7% by weight of N-methylpyrrolidone and 8.3% by weight of water and an S/M ratio of circulating solvent S to feed M of C4-hydrocarbon mixture of 12.74 is maintained. This means that to achieve the same degree of success of the separation in the Comparative Experiment accompanying Example 2 as in Example 2 itself, the S/M ratio had to be 93% higher.

EXAMPLE 3

The procedure described in Example 1 and the corresponding Comparative Experiment is followed, except that in Example 3 the selective solvent is a mixture of 90% by weight of N-methylpyrrolidone and 10% by weight of ethyl acetate and the S/M ratio of circulating solvent S to feed M of C4-hydrocarbon mixture is maintained at 6.72, whilst in the Comparative Example accompanying Example 3, the selective solvent is a mixture of 91.7% by weight of N-methylpyrrolidone and 8.3% by weight of water and an S/M ratio of circulating solvent S to feed M of C4-hydrocarbon mixture of 12.74 is maintained. Whilst in Example 3, starting from 0.658 kg/h of feed M containing 4.18% by weight of cis-but-2-ene and 42.58% by weight of 1,3-butadiene, 0.340 kg/h of raffinate containing 5.17% by weight of cis-but-2-ene and 2.47% of 1,3-butadiene, and 0.318 kg/h of crude butadiene containing 3.24% by weight of cis-but-2-ene and 76.75% by weight of 1,3-butadiene are obtained, the Comparative Experiment, in spite of using an S/M ratio which is almost 90% higher, gave, starting from 0.471 kg/h of feed M, containing 4.45% by weight of cis-but-2-ene and 41.98% by weight of 1,3-butadiene, 0.235 kg/h of raffinate containing only 4.41% by weight of cis-but-2-ene and still containing 14.77% by weight of 1,3-butadiene, and 0.236 kg/h of crude butadiene still containing 4.66% by weight of cis-but-2-ene and only 69.07% by weight of 1,3-butadiene.

We claim:
1. A process for isolating a conjugated diolefin from a C4- or C5-hydrocarbon mixture containing the diolefin, by extractive distillation using a selective solvent, wherein the selective solvent is a solvent mixture which comprises
    (a) from 50 to 98 percent by weight of a N-alkyl-substituted lower aliphatic acid amide or of a N-alkyl-substituted alicyclic acid amide having 5 ring members and
    (b) from 2 to 50 percent by weight of a lower aliphatic carboxylic acid ester or carbonic acid ester boiling at from 30° C. to 200° C.

2. A process as claimed in claim 1, wherein the solvent mixture used comprises
    (a) from 5 to 98 percent by weight of dimethylformamide, diethylformamide, dimethylacetamide, diethylacetamide, formylmorpholine or N-methylpyrrolidone and
    (b) from 2 to 50 percent by weight of a lower aliphatic carboxylic acid ester or carbonic acid ester boiling at from 30° C. to 200° C.

3. A process as claimed in claim 1 or 2, wherein the solvent mixture contains at most 5 percent by weight of water, based on solvent mixture.

* * * * *

UNITED STATES PATENT AND TRADEMARK OFFICE
CERTIFICATE OF CORRECTION

PATENT NO. : 4,277,315

DATED : July 7, 1981

INVENTOR(S) : K. Volkamer, K. Broellos, A. Lindner, U. Wagner, H. Weitz, and K. Schneider It is certified that error appears in the above—identified patent and that said Letters Patent is hereby corrected as shown below:

On Claim 2(a), line 55, "5" should read --50--.

Signed and Sealed this

Third Day of November 1981

|SEAL|

Attest:

GERALD J. MOSSINGHOFF

Attesting Officer

Commissioner of Patents and Trademarks